United States Patent [19]

Klodowski

[11] Patent Number: 4,923,806
[45] Date of Patent: May 8, 1990

[54] METHOD AND APPARATUS FOR REFRIGERANT TESTING IN A CLOSED SYSTEM

[75] Inventor: Harry F. Klodowski, E. Syracuse, N.Y.

[73] Assignee: Carrier Corporation, Syracuse, N.Y.

[21] Appl. No.: 32,106

[22] Filed: Mar. 27, 1987

Related U.S. Application Data

[63] Continuation-in-part of Ser. No. 746,491, Jun. 14, 1985, abandoned.

[51] Int. Cl.$^5$ .................... G01N 31/22; G01N 33/18
[52] U.S. Cl. .......................... 436/39; 62/127; 62/128; 422/58; 422/86; 422/104; 436/41; 436/100; 436/167
[58] Field of Search .............. 422/58, 86, 104; 436/39, 41, 100, 167; 62/125, 127, 128, 129

[56] References Cited

U.S. PATENT DOCUMENTS

| | | | |
|---|---|---|---|
| 2,429,694 | 10/1947 | King | 436/39 |
| 3,127,246 | 3/1964 | Carroll | 422/86 |
| 3,539,302 | 11/1970 | Dreckmann | 436/122 X |
| 3,625,656 | 12/1971 | Paulson | 422/86 |
| 4,018,061 | 4/1977 | Williamitis | 62/125 |
| 4,022,578 | 5/1977 | Kretschner | . |
| 4,259,287 | 3/1981 | Leichnitz | 422/60 X |
| 4,271,125 | 6/1981 | Leichnitz | 422/60 X |
| 4,300,910 | 11/1981 | Pannwitz | 422/60 X |
| 4,329,153 | 5/1982 | Leichnitz | 422/86 X |
| 4,330,297 | 5/1982 | Leichnitz | 422/60 X |
| 4,389,372 | 6/1983 | Lalin | 422/88 |
| 4,460,544 | 7/1984 | Leichnitz | 422/60 X |

*Primary Examiner*—Barry S. Richman
*Assistant Examiner*—Jill Johnston
*Attorney, Agent, or Firm*—David J. Zobkiw

[57] ABSTRACT

In a preferred embodiment, refrigerant together with oil, water and any other contaminants is drawn off from a high pressure refrigeration system. The drawn off refrigerant is reduced in pressure and serially, the oil is removed, the water is removed and the amount of water and acid present is determined.

11 Claims, 3 Drawing Sheets

METHOD AND APPARATUS FOR REFRIGERANT TESTING IN A CLOSED SYSTEM

This application is a continuation-in-part of application Ser. No. 746,491 which was filed on June 14, 1985 and is now abandoned.

BACKGROUND OF THE INVENTION

A number of saturated fluorocarbon compounds and azeotropes are commonly used as refrigerants in refrigeration systems. The various refrigerants have different physical constants, such as boiling points and vapor pressures, which dictate their suitability for a particular use. Refrigerant systems are generally classified as either high pressure or low pressure depending upon the contained pressure. In many refrigeration systems a small amount of oil is circulated with the refrigerant and its presence is considered in the designing of the systems. Also, refrigerants and oil absorb moisture to a degree so that some water is usually present. The refrigerant goes between the liquid and vapor states in the refrigeration cycle. Contaminants in the refrigerants may also be considered as liquid or vapor in that their dew points are relatively close to those of the refrigerants and can possibly condense and vaporize in the cycle. To treat a contamination problem, it is first necessary to identify the contaminant(s) present. In testing refrigerants in a closed system, it can thus be generally assumed that the refrigerant, at ambient temperature, can be at a pressure ranging from about 20 psig to over 200 psig, depending upon the refrigerant, and that some oil and water will be present. In addition, contaminants such as the reaction products of the chemical reactions between the refrigerant, lubricant, moisture, residual solvents, solder, flux, electrical insulation materials, etc. may be present and the contaminants and refrigerant may be in the liquid or vapor state. If a closed refrigeration system is to be tested to determine the presence of contaminants, the normal procedure is to remove the refrigerant from the system and test it for water. The lubricant from the compressor is tested for acids, etc. in a separate test.

The presence of excess moisture in the system can be due to faulty drying of equipment at the factory and in service operations, leaks in the system, oxidation of hydrocarbons, wet oil and/or refrigerant and decomposition of cellulose insulation in hermetically sealed units. The presence of excess moisture can cause ice formation in the expansion valves and capillary tubes, corrosion of metals, copper plating and chemical damage to insulation in hermetic compressors. Acid can be present due to motor burnouts which cause overheating of the refrigerant. Such burnouts can be temporary or localized in nature as in the case of a friction producing chip which causes a local hot spot which overheats the refrigerant. The main acid of concern is HCl but other acids and contaminants can be produced as the decomposition products of oil, insulation, varnish, gaskets and adhesives.

SUMMARY OF THE INVENTION

The present invention is directed to a method and apparatus for quantitatively testing refrigerants in a closed system for the presence of a plurality of contaminants in a single test without withdrawing more refrigerant than is needed for the test. The test is valid whether the contaminants are liquid or vapor, whether the system is operating or not, and is adaptable for high or low pressure usage.

It is an object of this invention to provide a method and apparatus for detecting liquid and gaseous contaminants in the refrigerant in a closed system without removing all of the refrigerant from the system.

It is another object of this invention to remove oil from the refrigerant in the detecting apparatus prior to the refrigerant contacting the indicating layers.

It is an additional object of this invention to provide a method and apparatus for testing a hermetic compressor, whether failed or operating, without disassembly, to determine the mode of failure or the condition of the system.

It is another object of this invention to determine the presence of strong acids in refrigerants.

It is another object of this invention to determine the acidity of a hermetically sealed compressor without requiring the dumping of the refrigerant charge.

It is a further object of this invention to provide a single test for multiple contaminants in a refrigerant. These objects, and others as will become apparent hereinafter, are accomplished by the present invention.

Basically, the present invention is directed to a method and apparatus for detecting contaminants in a refrigerant medium. The single use transparent glass testing tube is sealed until used and contains therein an oil removal section, a water removal and indicating section and an acid indicating section. In use, the ends of the glass testing tube are broken off and the tube is placed in a tube holder apparatus which functions to seal the tube so that all of the refrigerant flow is directed through the tube, provides a protective shield for the tube and, if necessary, throttles down the pressure reaching the tube. The presence of contaminants is indicated by a color change which can be quantified by comparison to a color chart and/or the extent of the propagation of the color change in the indicating media.

BRIEF DESCRIPTION OF THE DRAWINGS

For a fuller understanding of the present invention, reference should now be made to the following detailed description thereof taken in conjunction with the accompanying drawings wherein.

DESCRIPTION OF THE PREFERRED EMBODIMENTS

Figure 1:
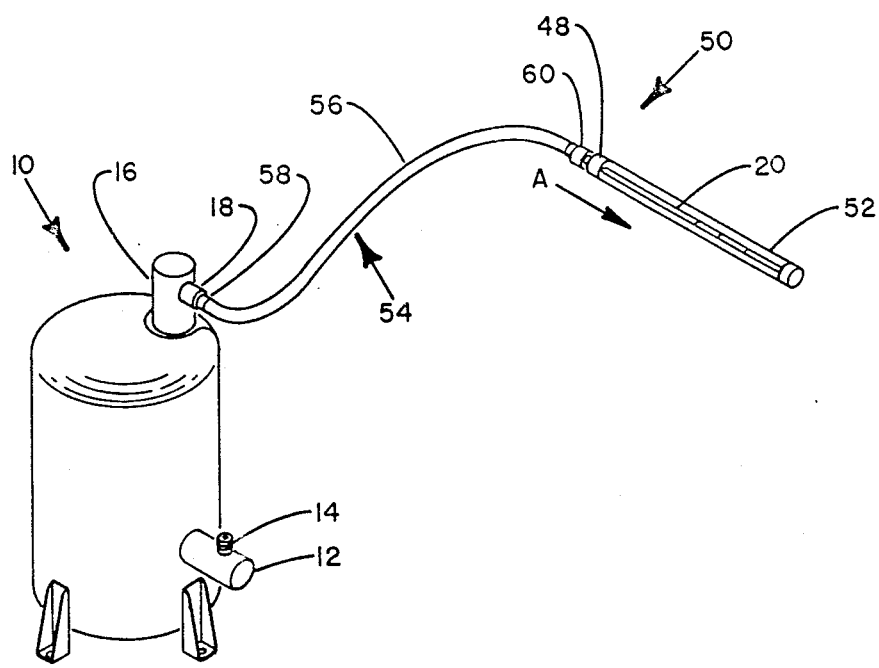
FIG. 1 is a perspective view of a preferred embodiment of the present invention in use with a portion of a refrigeration, air conditioning or similar system for conditioning air.

Referring to FIG. 1, there is illustrated one embodiment of the present invention being used in conjunction with a compressor 10 of a refrigeration, air conditioning, or similar closed system that utilizes a compressor for compressing a refrigerant. Compressor 10 has a suction line 12 with a service valve 14 therein, and a discharge line 16 with a service valve 18 therein. The present invention is illustrated being used to test for the presence of contaminants in the refrigerant vapor leaving compressor 10 via discharge line 16 but the present invention contemplates sampling a portion of the refrigerant vapor at other points in the system such as the suction line 12 of compressor 10. Moreover, the present invention can also be used to test for contaminants in other types of systems wherein the fluid is maintained either at relatively high pressure or at ambient pressure.

Figure 2:
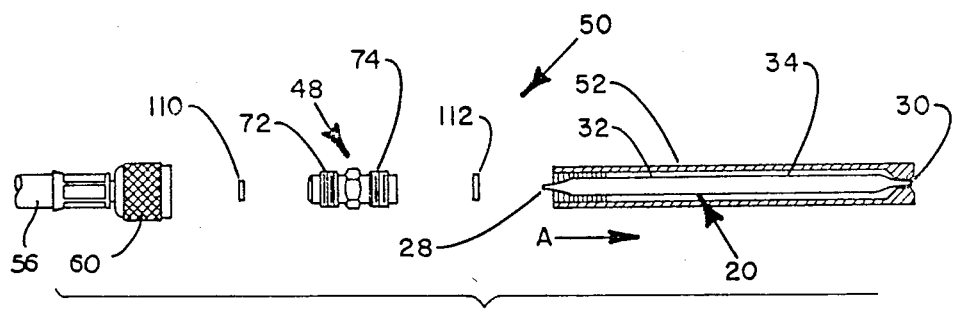
FIG. 2 is a partially exploded view of a refrigerant vapor testing tube holder apparatus and a multiple contaminant testing tube of the embodiment in FIG. 1.
Figure 3:
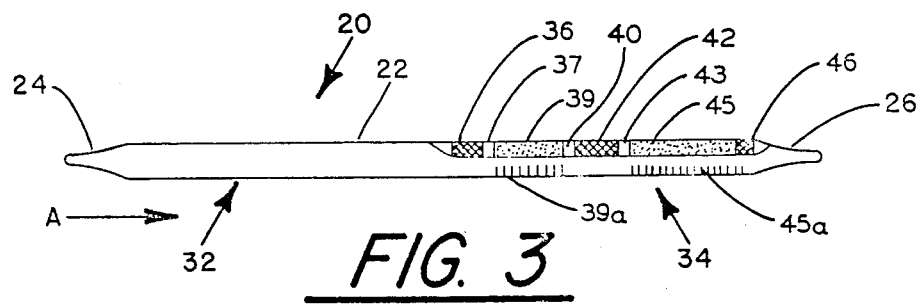
FIG. 3 is a partially cutaway side elevational view of the multiple contaminant testing tube in FIG. 2.

Referring primarily to FIG. 3, there is illustrated a disposable multiple contaminant testing tube 20 for detecting the presence of contaminants in a refrigerant vapor, such as water and acids. In this particular embodiment, testing tube 20 is designed to test for two particular contaminants in a refrigerant vapor. Testing tube 20 comprises a generally cylindrical tube 22 made of a transparent material, such as soda-lime glass or other suitable material. Tube 22 has oppositely disposed tapered ends terminating in frangible upstream tip 24 and frangible downstream tip 26. These tips 24 and 26 are designed to be broken, for use, to thereby define upstream open end 28 and downstream open end 30 (FIG. 2), and are generally conical in shape.

Testing tube 20 is generally divided into a demister section 32 for oil removal and contaminant-indicating section 34. In a preferred embodiment, tube 22 is 130 mm in overall length and 105 mm in length excluding the tapers at the tips. The inside and outside diameters are 4 mm and 6 mm, respectively. In the assembled tube 20, the demister section 32 would extend from upstream end 24 for about half the length of tube 22 and is essentially an open section permitting entrained oil to settle out prior to reaching the contaminant-indicating section 34. Oil separation is enhanced if flow through tube 22 is vertically upward. Starting at the upstream end of the contaminant-indicating section 34, tube 22 serially contains a 3 mm length of brass screen 36, a 1 mm thick glass fiber disc 37, a 12 mm long water removal and moisture indicating section 39, a 1 mm thick glass fiber disc 40, an 8 mm length of rolled brass screen 42, a 1 mm thick glass fiber disc 43, a 25 mm long acid indicating section 45 and a 3 mm length of brass screen 46. The chemicals making up the water removal and moisture indicating section 39 and the acid indicating section 45 are located in the tube 22 relative to indicia 39a and 45a, respectively, or the indicia 39a and 45a are placed on tube 22 after tube 22 is sealed. Partitioning discs 37, 40 and 43 can be made of any suitable material in addition to fiberglass such as metal, or plastic material and primarily serve as wadding to keep the chemicals in place as well as providing physical separation for the chemicals. The amounts or the thickness of any disc is dependent upon the type of substances it separates, the dimensions of tube 22, and the like. The primary function of screen or filter members 36, 42 and 46 is to maintain the indicating media in indicating sections 39 and 45 and discs 37, 40 and 43 in place in contaminant-indicating section 34 as well as providing, in the case of screen 42, physical separation for the chemicals as well as discs 37, 40 and 43. Screen or filter members 36, 42 and 46 inherently screen or filter out particulate matter, but are not intended to filter out any contaminants desired to be detected in indicating sections 39 and 45. Naturally, should the screen or filter members or the discs filter out any of the contaminants to be detected, then indicating sections 39 and 45 could indicate inaccurate amounts of contaminants present in the refrigerant vapor. Screen or filter members 36, 42 and 46 can be made of metal, glass, plastic, ceramic, and the like, in addition to the preferred brass.

Disposed on the outer surface of contaminant-indicating section 34 are a series of indicia 39a and 45a for readily determining the length of the color change in respective indicating sections 39 and 45. The distance between individual marks making up indicia 39a and 45a is empirically determined based upon the type of indicating substance, the dimensions of tube 22, the granularity of the particular indicating substance, and the like. Indicia 39a and 45a can be disposed on tube 22 by means of adhesive tape, etching, or the like.

If desired, indicia 39a can be eliminated and the water concentration determined by the color change of the entire indicating section 39. The indicating of the amount or concentration of contaminant(s) is then done with the use of a color-coded card. For example, matching the shade of color of the changed indicating substance with the same shade on the color-coded card can indicate the concentration or amount of contaminant present, wherein each shade of color on the card represents a predetermined concentration of contaminant. Further, the color codes can also indicate a particular servicing procedure to be followed to remove the contaminant.

The water removal and moisture indicating media in section 39 can be suitably prepared as follows:

MOISTURE INDICATING CHEMICAL

The following procedure describes the steps required to prepare the moisture indicating chemical used in the contaminant tester tube. Cobaltous chloride is used as the indicator, and turns from blue to pink when exposed to moisture. Two coats of the cobaltous chloride are applied to the sand, then two chloroform washes are used to remove any excess chemical that would later flake from the sand particles. The sand is then stored in a tightly sealed jar until ready to use.

RECIPE FOR PREPARING MOISTURE INDICATING MEDIA

1. Weigh approximately 300 grams of silica sand (Fisher Catalog No. S-15U Mesh size 30-50) into a 600 milliliter beaker.
2. Add to the beaker a solution of 30% cobaltous chloride in acetone until the sand is just covered.
3. Stir gently until all sand has reacted with the cobaltous chloride solution and then allow to stand for approximately one-half hour.
4. Decant liquid. Pour sand into a large flat casserole dish.
5. Heat sand on hot plate until dry with constant stirring (sand will change in color from pink to lavender to blue when completely dry.)
6. To apply a second coat of the chemical to the sand, repeat steps 2-5, then proceed to step 7.
7. Transfer sand to a clean 500 ml beaker when cool.
8. Add chloroform to beaker until sand is just covered and stir gently.
9. Decant chloroform. (This removes excess cobaltous chloride fines from the sand.)
10. Dry sand (as described in step 5).

11. For second chloroform washing, repeat steps 7–10. Then go on to next step.
12. Store dry, blue sand in tightly sealed jar.

Note—If sand begins to change color (blue to lavender to pink), heat sand on hot plate with constant stirring until blue color returns.

The acid indicating media in section 45 which is suitable for detecting all mineral acids is prepared as follows starting with a freshly made stock indicator solution of 400 mg of bromophenol blue, 98 ml of ethanol and 2 ml of glycerol which have been stirred until dissolved:

PROCEDURE

1. Weigh 100 grams of sieved silica into a 250 ml beaker with a Teflon stir bar.
2. Add 75 ml of 0.5% polyethlene glycol solution which has been neutralized to a pH of 6.5–7.0 using 0.01 N NaOH.
3. Heat on a stirring hot plate to a gentle boil and boil for 5 min., cool and recheck pH.
4. Decant solution and add deionized water (50 ml) and reheat to a boil. Simmer for 1 minute.
5. Decant solution and allow ample time for the excess to drain.
6. Dry the treated silica on a tray or dish in a 100 degree centigrade oven.
7. Cool and transfer to a 500 ml side-arm vacuum flask.
8. Treat the silica with indicator solution—2 ml of solution per 100 grams of silica. Make two applications (approximately 1 ml each).
9. Solvent is evaporated using a vacuum pump and a liquid nitrogen cold trap.
10. Pumping is continued 15 minutes beyond the time when the media is free flowing and appears dry. Excessive pumping will remove glycerol film from the media. It will be noted that this indicator is on a nonaqueous base and that the base is silica (sand) covered by glycerol rather than silica gel. An aqueous base is much less sensitive to acid and a silica gel base can give an acidic indication if allowed to react with the bromophenol blue.

Referring again to FIG. 3, it will be noted that water removal and moisture indicating section 39 is reached by the entering gas only after serially passing through demister section 32, brass screen 36 and glass fiber disc 37. The water removal and moisture indicating section 39 is separated from the acid indicating section 45 by glass fiber disc 40, rolled brass screen 42 and glass fiber disc 43 to isolate and separate the indicating media in the sealed tube prior to use and thereby prevent migrational action therebetween. So with the tips 24 and 26 of tube 20 sealed and unbroken, as illustrated in FIG. 3, the water removal and indicating section 39 and acid indicating section 45 are effectively separated from each other and are isolated from the environment until the tips are broken.

The present invention is suited for use in detecting contaminants in fluids maintained at a relatively high pressure. For example, in a refrigeration, air conditioning, or similar system, the refrigerant can be maintained at relatively high pressures, such as 200 lbs. per square inch. Furthermore, since the refrigerant vapor generally has lubricant vapors entrained therein, prior to testing the refrigerant vapor for contaminants, it is highly desirable to separate and remove any entrained lubricant. The separation of entrained lubricant from the refrigerant is accomplished by means of demister section 32 in conjunction with flow restrictor 48, a more detailed description of which will follow. Basically, flow restrictor 48 is designed to reduce the pressure of the refrigerant vapor from its relatively high system pressure to a relatively low pressure before the refrigerant vapor enters testing tube 20. As the refrigerant vapor passes through flow restrictor 48, it is reduced from its relatively high pressure to a relatively low pressure and virtually immediately thereafter enters demister section 32 through upstream open end 28. Because of the rapid decrease in pressure, the entrained lubricant vapors separate from the refrigerant vapor and collect on the side of demister section 32 in the form of minute droplets. The length of demister section 32 can vary and may be dependent upon the pressure differential between the system pressure and ambient pressure, the dimensions of tube 22, the anticipated amount of entrained lubricant in the vapor, and the like. As is clear from the preceding commentary, the direction of flow of refrigerant vapor through multiple contaminant testing tube 20 is in the direction of arrow A which appears in FIGS. 1–4.

Referring now to FIGS. 1, 2, 4 and 5, refrigerant vapor testing tube holder apparatus 50 is illustrated with a multiple contaminant testing tube 20 therein for testing fluids maintained at a relatively high pressure. Testing tube holder apparatus 50 generally comprises tube container 52, flow restrictor 48 and fluid hose 54, which may be a standard refrigerant hose. Fluid hose 54 includes a hose line 56 having on one end thereof connector 58, which may be a Schraeder type fitting, for connection to service valve 18, and a connector 60 at the other end for connecting to flow restrictor 48.

Figure 4:
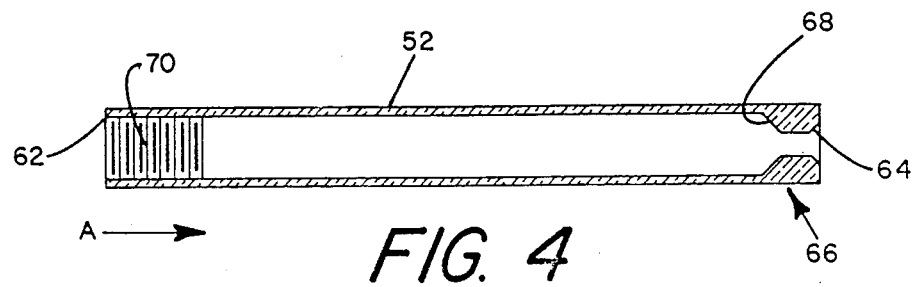
FIG. 4 is a longitudinal sectional view of a tube container in the refrigerant vapor testing tube holder apparatus in FIG. 2.

Referring primarily to FIG. 4, tube container 52 is made of a generally transparent material such as Plexiglas and is of sufficient inner diameter to contain testing tube 20, as illustrated in FIGS. 1 and 2. Tube container 52 includes oppositely disposed upstream open end 62 and downstream open end 64. Naturally, all references to elements or voids as being upstream or downstream is in relation to arrow A indicating the flow direction of the fluid being tested. Located at downstream open end 64 is support means or member 66. Member 66 includes a continuous beveled surface 68 sloping radially inwardly and axially outwardly for centrally supporting therein the generally conically-shaped downstream open end 30 of testing tube 20. Other types of support can be used to centrally locate downstream open end 30 in tube container 52. Upstream open end 62 has an internally threaded surface portion 70 for connection to flow restrictor 48.

Figure 5:
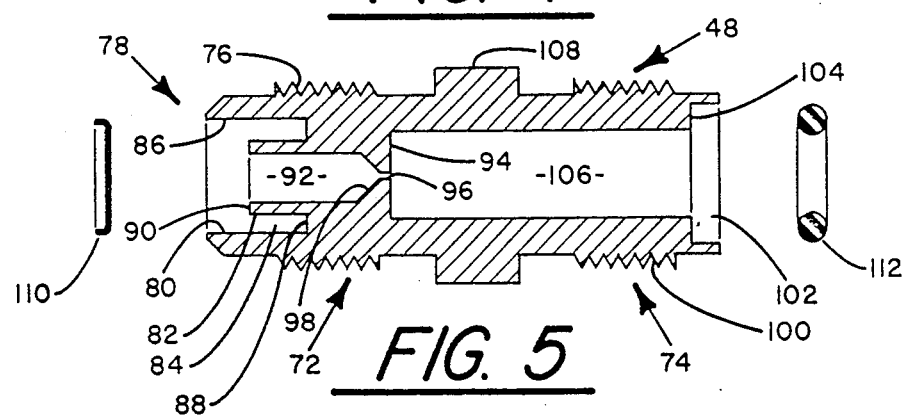
FIG. 5 is an enlarged and exploded view in cross section of the flow restrictor in the refrigerant vapor testing tube holder apparatus in FIG. 2.

Referring now to FIG. 5, flow restrictor 48 is a somewhat elongate body having oppositely disposed end sections 72 and 74.

End section 72 includes a threaded surface 76 for threadedly attaching flow restrictor 48 to connector 60 of fluid hose 54, and pressure-reducing means 78 disposed just downstream of opening 80. Pressure-reducing means 78 includes a collar section 82 spaced axially and radially inwardly of opening 80 to define annular space 84 between inner surface 86 and the outer surface of collar section 82. Collar section 82 also defines annular bottom surface 88, annular remote end surface 90, and passage 92. Pressure-reducing means 78 further comprises a wall member 94 at the innermost end of passage 92 with a small orifice 96 disposed therein. In this embodiment, the diameter of orifice 96 is of a predetermined dimension to provide a refrigerant vapor flow of about 300 cc/min when operating at a refrigerant pressure of about 125 psi. Within passage 92 is a continuous beveled surface 98 that slopes radially inwardly and axially inwardly towards wall member 94 and defining the entrance to the orifice 96. Pressure-reducing means 78 can be designed to produce greater or lesser flows, or to produce the same flow at higher or lower refrigerant pressures.

End section 74 includes an externally threaded surface 100 for threadedly attaching flow restrictor 48 to threaded surface portion 70 of tube container 52. End section 74 further includes opening 102, an annular groove 104, and a passage 106 in fluid communication with passage 92 through orifice 96. The outer surface of end section 74 also includes a hex nut flange 108 to assist in manually connecting flow restrictor 48 to fluid hose 54 and tube container 52. As illustrated, passage 106 is larger in diameter than passage 92.

A vapor-permeable screen or filter 110 is disposed in opening 80 of end section 72 and rests against annular remote end surface 90 of collar section 82. On the opposite end of flow restrictor 48, a seal, such as O-ring 112, is securely fitted in annular groove 104 and serves to provide a fluid-tight fit between flow restrictor 48 and the conically-shaped upstream open end 28 of testing tube 20 such that all of the flow goes through tube 20. Regarding screen or filter 110, it is designed to filter out of the refrigerant vapor only particulate matter not intended to be detected in indicating sections 39 and 45 and to prevent clogging of orifice 96.

Alternatively, flow restrictor 48 or pressure-reducing means 78 could be disposed in connector 58 of hose line 56 to provide the desired refrigerant vapor flow rate through line 56 and tube 20; or, pressure-reducing means 78 could be disposed at downstream open end 64 of tube container 52.

In operation, when it is desired to detect any contaminants in a refrigerant vapor maintained at a relatively high pressure in a refrigeration, air conditioning, or other system, disposable multi-contaminant testing tube 20 is provided having the desired indicating media in indicating sections 39 and 45 for indicating the contaminants desired to be detected. Breakable upstream and downstream tips 24 and 26 of testing tube 20 are broken in any conventional manner to produce open ends 28 and 30, respectively, and testing tube 20 is then inserted manually in tube container 52 so that downstream open end 30 is supported by continuous beveled surface 68 of support member 66. Flow restrictor 48, with screen 110 and 0-ring 112 fitted therein, is threadedly engaged by means of its end section 74 in threaded surface portion 70 of tube container 52. Care should be taken at this time to ensure that upstream open end 28 of testing tube 20 is received within 0-ring 112, so as to ensure a fluid-tight fit and prevent bypassing of tube 20. Flow restrictor 48 is then manually hand-tightened to tube container 52 until testing tube 20 is secured therein and 0-ring 112 is closely fitted between flow restrictor 48 and testing tube 20.

Thereafter, end section 72 of flow restrictor 48 is manually threadedly connected to connector 60 of hose line 56. Hose line 56 is then connected to compressor 10 by manually threadedly connecting Schraeder connector 58 to suction line service valve 18. It is necessary to purge the test apparatus before use so that if assembled and attached to the compressor 10, as described, but with tube 20 removed and intact the entire apparatus can be purged. At a minimum, hose line 56 must be purged. Purging only requires a flow of refrigerant for a short time.

With the apparatus purged and connected as described, the relatively high pressure refrigerant vapor then flows through hose line 56 into flow restrictor 48. Because of pressure-reducing means 78, flow resistance is increased thereby decreasing the flow rate, and the pressure of the refrigerant vapor passing through pressure-reducing means 78 is reduced. This reduction in pressure of the refrigerant vapor is accomplished initially by collar section 82 and annular space 84, which reduces the flow area for the incoming refrigerant vapor. The refrigerant vapor continues through passage 92 which is reduced in cross section by continuous beveled surface 98 and orifice 96. The refrigerant vapor that flows through orifice 96 into passage 106 has been reduced from its system pressure to an acceptable pressure and flow rate. This reduced-pressure refrigerant vapor then flows through opening 102 into testing tube 20 through its upstream open end 28 and out therefrom through its downstream open 30.

Because of the large and rapid reduction in pressure of the refrigerant vapor as it passes through orifice 96 into demister section 32 of testing tube 20, any entrained lubricant in the vapor is separated therefrom due to the pressure reduction and is collected along the inner surface of demister section 32 in the form of minute droplets. The refrigerant vapor and all entrained contaminants then continue in the direction of arrow A serially through screen 36, disc 37, water removal and moisture indicating section 39, disc 40, screen 42, disc 43, acid indicating section 45 and screen 46 and out downstream open end 30.

TABLE I

| WATER VAPOR |
| --- |
| 1 MINUTE INDICATES ABOUT 800 PPM |
| 3 MINUTES INDICATES ABOUT 270 PPM |
| 5 MINUTES INDICATES ABOUT 160 PPM |
| 10 MINUTES INDICATES ABOUT 80 PPM |

TABLE II

| | ACIDS APPROXIMATE PPM | | | |
| --- | --- | --- | --- | --- |
| MARKER | SAMPLING TIME | | | |
| NUMBER | 1 MIN. | 3 MIN. | 5 MIN. | 10 MIN. |
| 1 | 0.2 | 0.06 | 0.04 | 0.02 |
| 2 | 0.3 | 0.10 | 0.06 | 0.03 |
| 3 | 0.4 | 0.13 | 0.08 | 0.04 |
| 4 | 0.5 | 0.20 | 0.11 | 0.05 |
| 5 | 0.6 | 0.21 | 0.13 | 0.06 |
| 6 | 0.8 | 0.26 | 0.15 | 0.08 |

After a predetermined amount of time, which ordinarily should be no more than ten minutes since each test should not require recharging the system, Schraeder connector 58 is disconnected from suction line service valve 18, and testing tube 20 is immediately withdrawn from tube container 52. Any water or strong acid contaminants in the refrigerant vapor will be indicated in indicating sections 39 and 45, respectively. The bromophenol blue in acid indicating section 45 will change from blue to yellow in the presence of mineral acids. The length of the color change is measured by counting the number of concentration units in indicia 45a along the changed color length and is then entered into Table II. Assuming the acid changes the bromophenol blue to yellow a distance equal to four concentration units of indicia 45a, then Table II is entered under the column designated Marker No. at the number 4 and then read across under the column indicating the predetermined time the refrigerant vapor was allowed to flow through testing tube 20. If in this example, the flow was maintained during a period of three minutes, then the acid-indicating media in acid indicating section 45 would indicate a contamination level of acid of 0.20 parts per million. Similar tables can be empirically determined for water.

After completion of a test, hose line 56 and flow restrictor 48 can be purged for subsequent testing procedures, or disposed of and replaced with a new hose line 56 and a new flow restrictor 48, i.e., hose line 56 and flow restrictor 48 can be designed to be disposable, and can be made of a suitable material, such as a plastic material.

Table I illustrates another method of determining the amount or concentration of a contaminant, such as water vapor. In this method, the refrigerant vapor is allowed to flow through testing tube 20 until the color of the indicating substance such as the water-indicating substance in water indicating section 39 turns a particular color shade that matches a color-coded card (not shown). When the two colors match, the time required for the color change of the water-indicating substance is then entered into Table I. For example, should it take three minutes for the water-indicating substance to turn to the desired shade on the color-coded card, then the three minutes would indicate a contamination level of approximately 270 parts per million.

Figure 6:
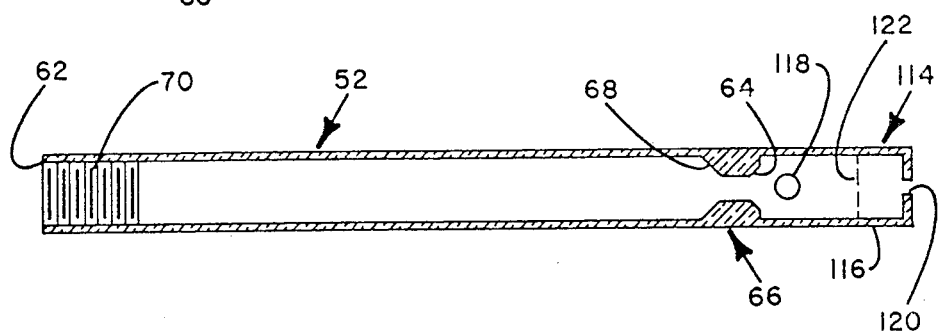
FIG. 6 is a longitudinal sectional view of a modified tube container.

Referring now to FIG. 6, tube container 52 is modified to include flow indicator 114 at downstream open end 64. Flow indicator 114 indicates to the serviceman that a proper flow rate of vapor exists to ensure accurate indications of any contaminants. Flow indicator 114 comprises a chamber 116, which can be integral with container 52 or made separately and then attached to container 52 by any suitable means, an indicator element such as pith ball 118, discharge opening 120, and flow line 122 disposed on chamber 116.

In operation, after connection to compressor 10, tube container 52 is held vertically with flow indicator 114 being upwardly disposed. If a proper vapor flow rate exists, it will cause ball 118 to be urged upwardly to flow line 122. If ball 118 does not reach line 122, then the vapor flow rate is less than desirable. This can be attributed to a blockage in the system or the like and after being remedied, the test can proceed as described above.

Ball 118 has a diameter greater than that of open end 64 and opening 120, and can be made of any suitable, lightweight material. Further, flow indicator 114 can be a separate device which the serviceman can use by merely holding it in place manually, to engage open end 64 and direct all of the flow passing through open end 64 through the flow indicator.

Other means for indicating flow rate can be used, such as a thin filament. At a predetermined, acceptable flow rate, the filament can be designed to be parallel to the general direction of flow. Any non-parallel position of the filament indicates a less than desirable flow rate.

Figure 7:
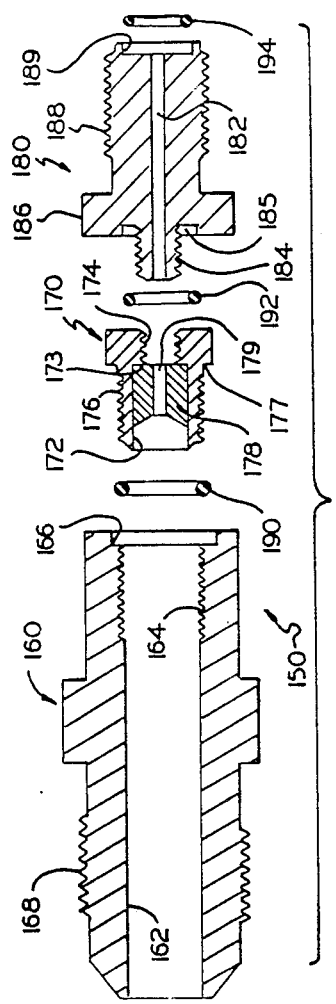
FIG. 7 is an exploded cross sectional view of a modified flow restrictor.

A modified flow restrictor assembly 150 is shown in FIG. 7 and includes orifice holder 160, retainer 170, cap 180 and 0-rings 190, 192, and 194. Orifice holder 160 has a bore 162 which includes a threaded section 164 terminating in an annular relieved portion 166. Threads 168 are formed on the exterior of orifice holder 160 and correspond to threads 76 of flow restrictor 48 and serve to permit connection of orifice holder 160 to connector 60. Orifice retainer 170 has a first bore 172 and a threaded second bore 174 with a shoulder 173 therebetween. A threaded portion 176 is formed on the exterior of orifice retainer 170 and terminates at shoulder 177. Threaded section 164 and threaded portion 176 can be threaded together so as to force 0-ring 190 into relieved portion 166 to form a fluid seal between orifice holder 160 and orifice retainer 170. Orifice 178 containing passage 179 is pressed into bore 172 and its passage 179 can be selected to provide a desired flow rate. Cap 180 has a bore 182 extending therethrough together with a first threaded portion 184, a second threaded portion 188, a hex nut flange 186 with an annular recess 185 formed therein. A second annular recess 189 is formed in the downstream end. First threaded portion 184 is threadedly received in threaded second bore 174 and forces 0-ring 192 into recess 185 so as to form a fluid seal between orifice retainer 170 and cap 180. Second threaded portion 188 corresponds to externally threaded surface 100 and is threadably engagable with threaded surface portion 70 of tube container 52. O-ring 194 coacts with recess 189 and conically-shaped upstream open end 28 of testing tube 20 to form a fluid seal so as to direct all of the flow going through bore 182 into tube 20. A filter (not illustrated) such as screen 110 must be located at any suitable location upstream of orifice 178.

In summary, refrigerant together with water, oil and other contaminants is drawn off from a closed refrigeration system and is passed at low/atmospheric pressure into the demister section of a contaminant testing tube where the oil is removed. The refrigerant and remaining contaminants then serially pass through a screen and a disc before reaching the water removal and indicating section. In the water removal and indicating section any water vapor present is removed and, if present, produces a color change whose distance of propagation is a measure of the water content. The removal of the water results in any mineral acids being present as anhydrous gases. The refrigerant and any acids then serially pass through a disc, a screen, and another disc before reaching the acid indicating section. The degree of separation between the water and acid indicating sections is due in part to the fact that the indicator media in the acid indicating section could react with the water indicating media if close enough. The strong acids react with the acid indicating media to produce a color change whose distance of propagation is a measure of the acid content. The finding of acid and excess water present in the refrigerant is the basis for replacing the refrigerant, adding conditioning items to the refrigeration system or determining the cause of failure in the system such as the burning out of the motor of a hermetic compressor where the burning of the insulation produces mineral acids which can also require the replacement of the compressor.

The maximum expected presence of water in refrigerant for residential and package air conditioners, for example, in ppm (mg/kg) by weight, is 15 for R-12 ($CCl_2F_2$) and 50 to 200 for R-22 ($CHClF_2$) Excess water could require the addition of driers to the system, locating and fixing leaks, etc. The presence of any acid requires replacement of the refrigerant if the system is otherwise operative as in the case of a temporary localized overheating caused by grit or the like which broke down some of the refrigerant.

Although preferred embodiments of the present invention have been illustrated and described in terms of an air conditioning system, it can be used for testing other high pressure systems. It is therefore, intended that the present invention is to be limited only by the scope of the appended claims.

What is claimed is:

1. A method of determining the presence of and the amount of contaminants present in refrigerants subject to contain oil, moisture and acids comprising the steps of:
   withdrawing a limited amount of refrigerant from a closed refrigeration or air conditioning system;
   reducing the pressure of the withdrawn refrigerant;
   serially taking the steps of:
   (a) removing any oil present in the withdrawn refrigerant;
   (b) removing any water present in the withdrawn refrigerant;
   (c) determining the amount of water present in the withdrawn refrigerant; and
   (d) determining the amount of acid present in the withdrawn refrigerant.

2. The method of claim 1 wherein said step of withdrawing a limited amount of refrigerant takes place continuously during the testing procedure.

3. The method of claim 1 wherein the testing procedure takes place while the closed refrigeration or air conditioning system is operating.

4. Multiple contaminant testing means for determining the presence and amounts of contaminants in refrigerants subject to contain oil, moisture and acids comprising:
   a testing tube;
   a testing tube holder apparatus for delivering in a flow of refrigerant from a closed refrigeration system to said testing tube wherein said testing tube holder apparatus comprises:
   (a) a generally elongate transparent container having oppositely disposed open ends, one of said open ends being an open inlet end and the other one of said open ends being an open outlet end, said container being adapted to removably contain therein said testing tube,
   (b) a coupling member connected to said open inlet end and having therein a passage in fluid communication with said container,
   (c) a sealing means being adapted for providing a fluid tight fit between said coupling member and said testing tube, and
   (d) a fluid pressure-reducing means adapted for reducing the pressure of said refrigerant;
   said testing tube comprising:
   (a) a single elongate tube member made of a generally transparent material and having oppositely disposed breakable ends, one of said ends being an inlet end and the other one of said ends being an outlet end, whereby said ends of said tube member can be broken to define respectively an inlet opening and an outlet opening,
   (b) an oil removal section adjacent said inlet end of said tube,
   (c) a first contaminant-indicating substance disposed in said tube member adjacent said oil removal section and adapted to remove and indicate the presence of water in said refrigerant,
   (d) a second contaminant-indicating substance disposed adjacent said first contaminantindicating substance and being adapted to indicate the presence of acid in said refrigerant, and
   (e) means disposed between said first and second contaminant-indicating substances for preventing migrational action therebetween.

5. The testing means of claim 4 wherein said fluid pressure-reducing means is an orifice.

6. The testing means of claim 4 further comprising a fluid-flow indicator means adapted for indicating a flow of fluid through said container.

7. The testing means of claim 6 wherein said fluid-flow indicating means comprises a chamber at said open outlet end of said container and in fluid communication therewith, said chamber having therein an opening and a fluid-flow responsive member movable by a predetermined fluid flow rate, whereby an acceptable fluid flow rate is indicated by the movement of said fluid-flow responsive member in said chamber.

8. The testing means of claim 4 wherein said means disposed between said first and second contaminant-indicating substances includes a pair of fluid permeable partitions separated by screen means.

9. The testing means of claim 4 wherein said first contaminant-indicating substance includes cobaltous chloride on a silica sand base.

10. The testing means of claim 4 wherein said second contaminant-indicating substance includes bromophenol blue on a glycerol film coating a silica sand base.

11. The testing means of claim 4 further comprising means for providing a fluid connection to a closed refrigeration or air conditioning system.

* * * * *